(12) United States Patent
Gupta et al.

(10) Patent No.: US 11,123,206 B2
(45) Date of Patent: Sep. 21, 2021

(54) KINK-RESISTANT STENT DEVICES AND RELATED METHODS

(71) Applicant: Monarch Biosciences, Inc., Los Angeles, CA (US)

(72) Inventors: Vikas Gupta, Los Angeles, CA (US); Colin Kealey, Los Angeles, CA (US)

(73) Assignee: Monarch Biosciences, Inc., Los Angeles, CA (US)

( * ) Notice: Subject to any disclaimer, the term of this patent is extended or adjusted under 35 U.S.C. 154(b) by 107 days.

(21) Appl. No.: 16/149,007

(22) Filed: Oct. 1, 2018

(65) Prior Publication Data

US 2019/0029852 A1 Jan. 31, 2019

Related U.S. Application Data

(63) Continuation of application No. PCT/US2017/025548, filed on Mar. 31, 2017.
(Continued)

(51) Int. Cl.
*A61F 2/91* (2013.01)
*A61F 2/915* (2013.01)
(Continued)

(52) U.S. Cl.
CPC .................. *A61F 2/91* (2013.01); *A61F 2/90* (2013.01); *A61F 2/915* (2013.01); *A61F 2002/823* (2013.01); *A61F 2210/0014* (2013.01); *A61F 2210/0057* (2013.01); *A61F 2210/0076* (2013.01); *A61F 2220/0058* (2013.01);
(Continued)

(58) Field of Classification Search
CPC ...... A61F 2/02; A61F 2/06; A61F 2/07; A61F 2/82; A61F 2/90; A61F 2/91; A61F 2/915; A61F 2002/823; A61F 2210/0014; A61F 2210/0057; A61F 2220/0058; A61F 2230/0013; A61F 2230/0021;
(Continued)

(56) References Cited

U.S. PATENT DOCUMENTS

2005/0283228 A1 12/2005 Stanford
2006/0136037 A1 6/2006 Debeer et al.
(Continued)

OTHER PUBLICATIONS

PCT Search Report and Written Opinion dated Jun. 15, 2017 from corresponding International Application No. PCT/US2017/025548 filed Mar. 31, 2017.

*Primary Examiner* — George J Ulsh
(74) *Attorney, Agent, or Firm* — Haynes and Boone, LLP

(57) ABSTRACT

A device includes an elastic tubular stent including struts forming closed cells arranged in rows along a circumferential direction of the stent, with each cell having a first obtuse-angled corner on one end of the cell along a longitudinal direction of the stent and a second obtuse-angled corner on an opposing end of the cell along the longitudinal direction. The stent may be fabricated by cutting an array of quadrilateral cells in a nitinol hypotube to form a stent, with each cell having four corners with approximately equal angles. The stent may then be expanded radially such that each cell has a first obtuse-angled corner on one end of the cell along a longitudinal direction of the stent and a second obtuse-angled corner on an opposing end of the cell along the longitudinal direction, and heat treated to fix the shape of the stent.

21 Claims, 13 Drawing Sheets

Related U.S. Application Data

(60) Provisional application No. 62/317,376, filed on Apr. 1, 2016.

(51) Int. Cl.
*A61F 2/90* (2013.01)
*A61F 2/82* (2013.01)

(52) U.S. Cl.
CPC ............... *A61F 2230/0013* (2013.01); *A61F 2230/0021* (2013.01); *A61F 2230/0073* (2013.01); *A61F 2240/002* (2013.01); *A61F 2250/0015* (2013.01); *A61F 2250/0023* (2013.01)

(58) Field of Classification Search
CPC ........ A61F 2230/0073; A61F 2240/002; A61F 2250/0015; A61F 2250/0023
See application file for complete search history.

(56) References Cited

U.S. PATENT DOCUMENTS

| | | | |
|---|---|---|---|
| 2009/0099644 A1 | 4/2009 | Biadillah et al. | |
| 2014/0012361 A1* | 1/2014 | Yamaguchi | A61F 2/958 623/1.11 |

\* cited by examiner

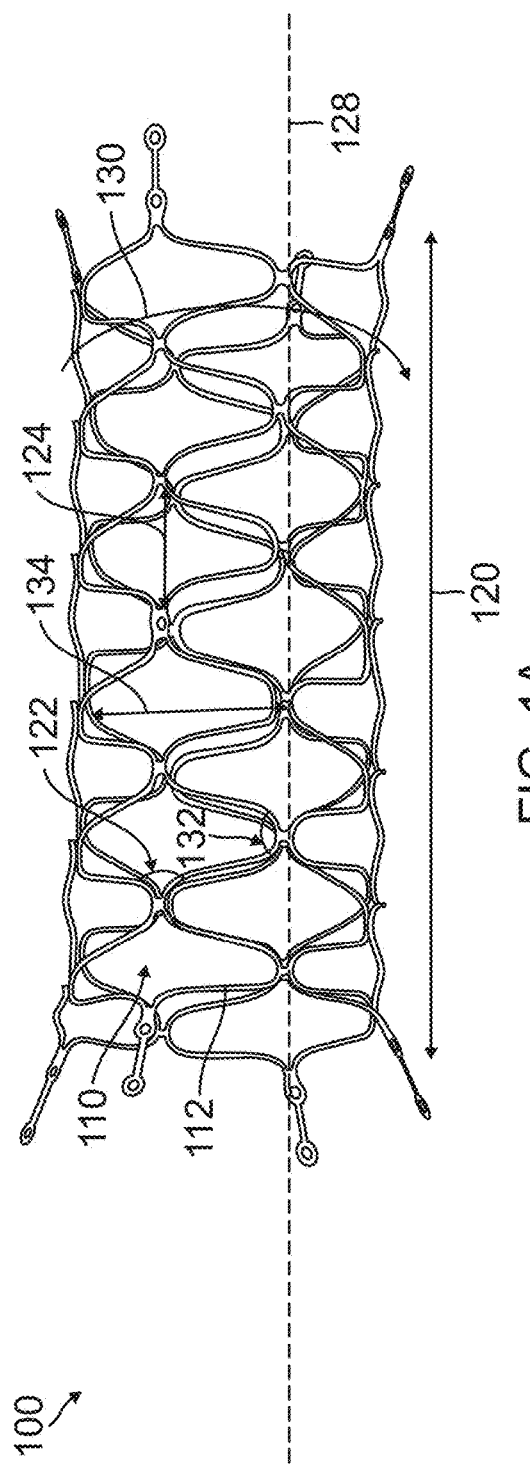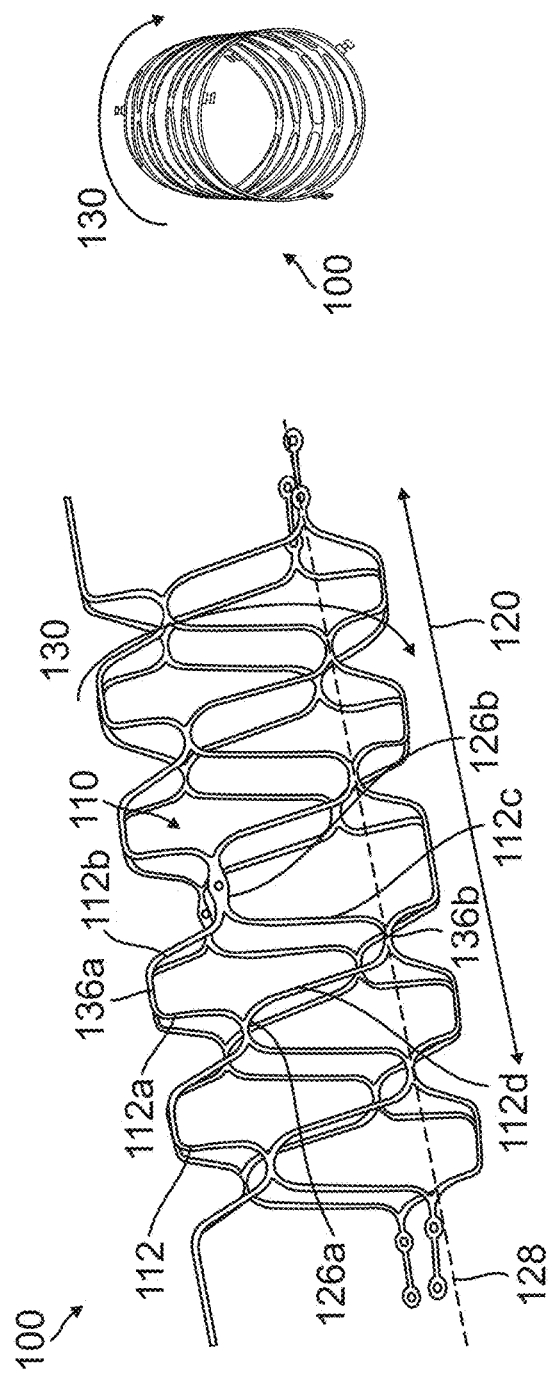

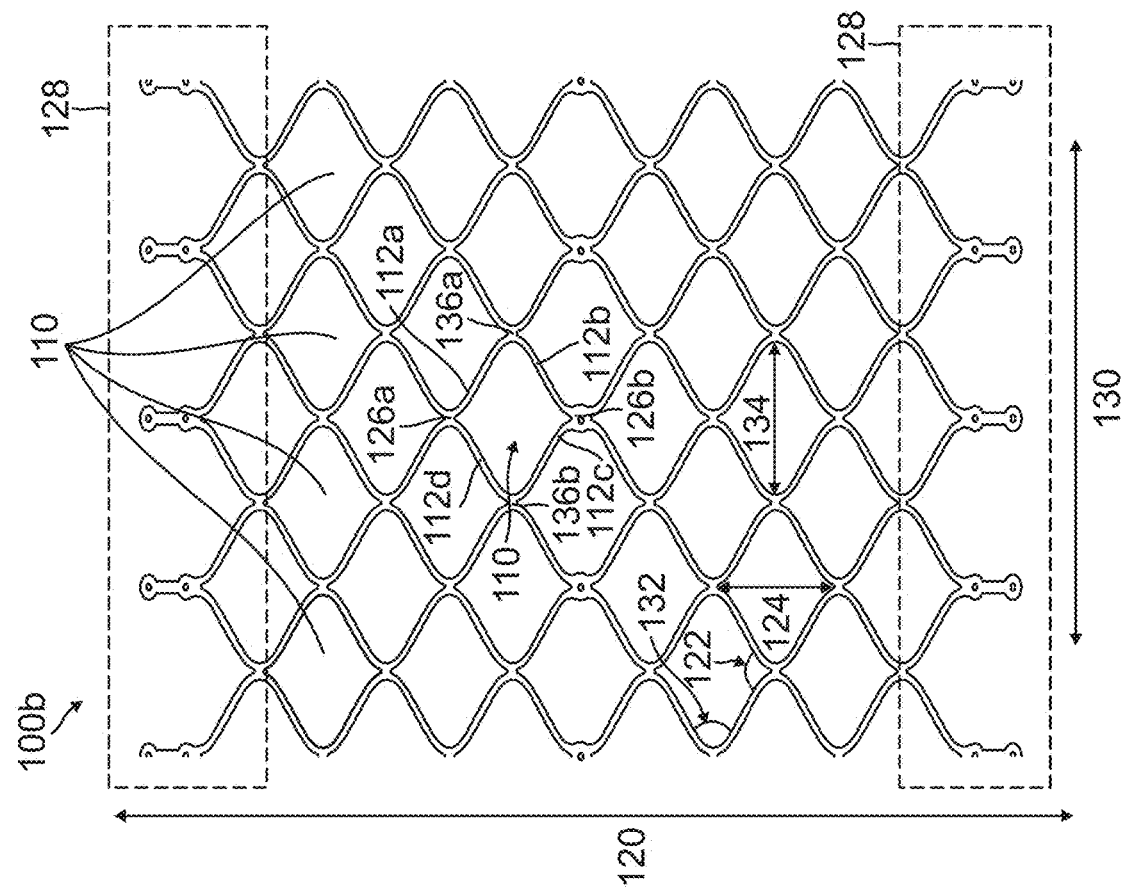
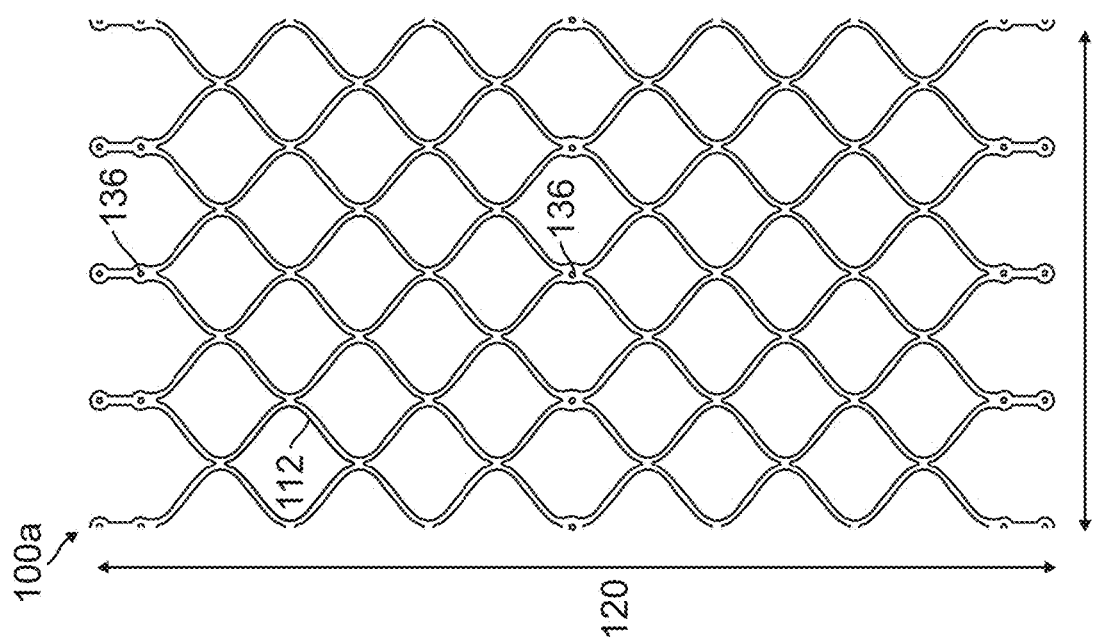

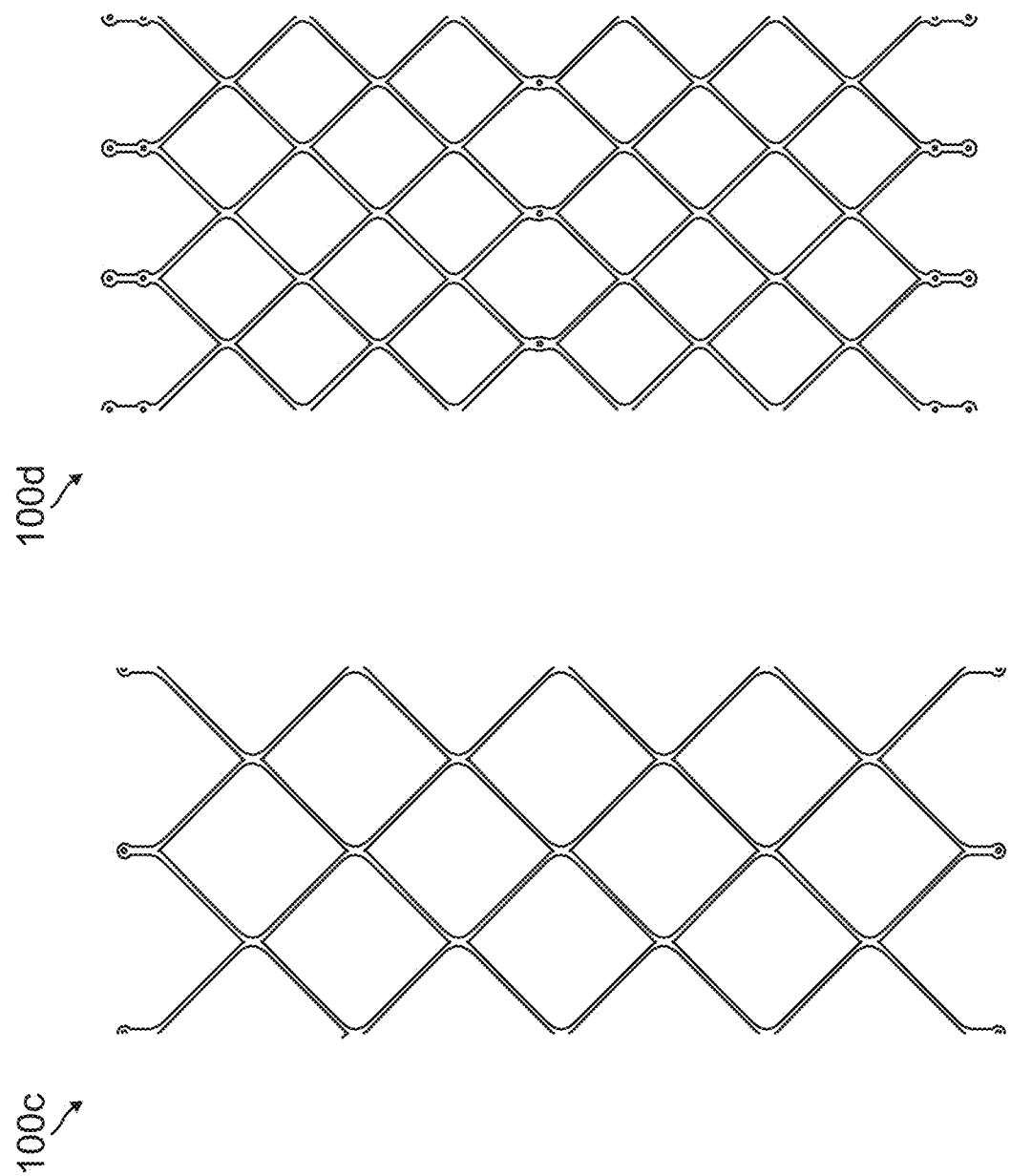

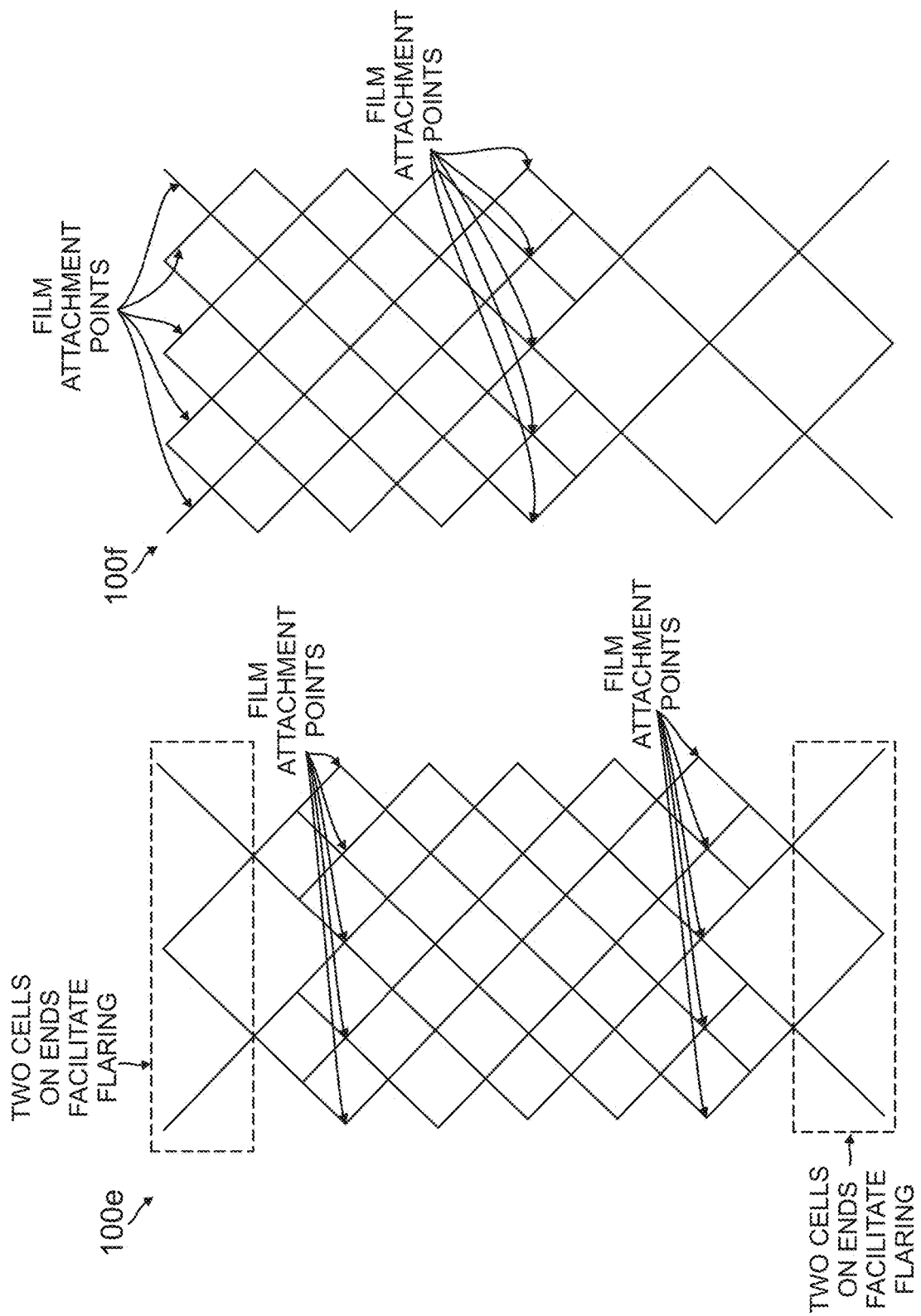

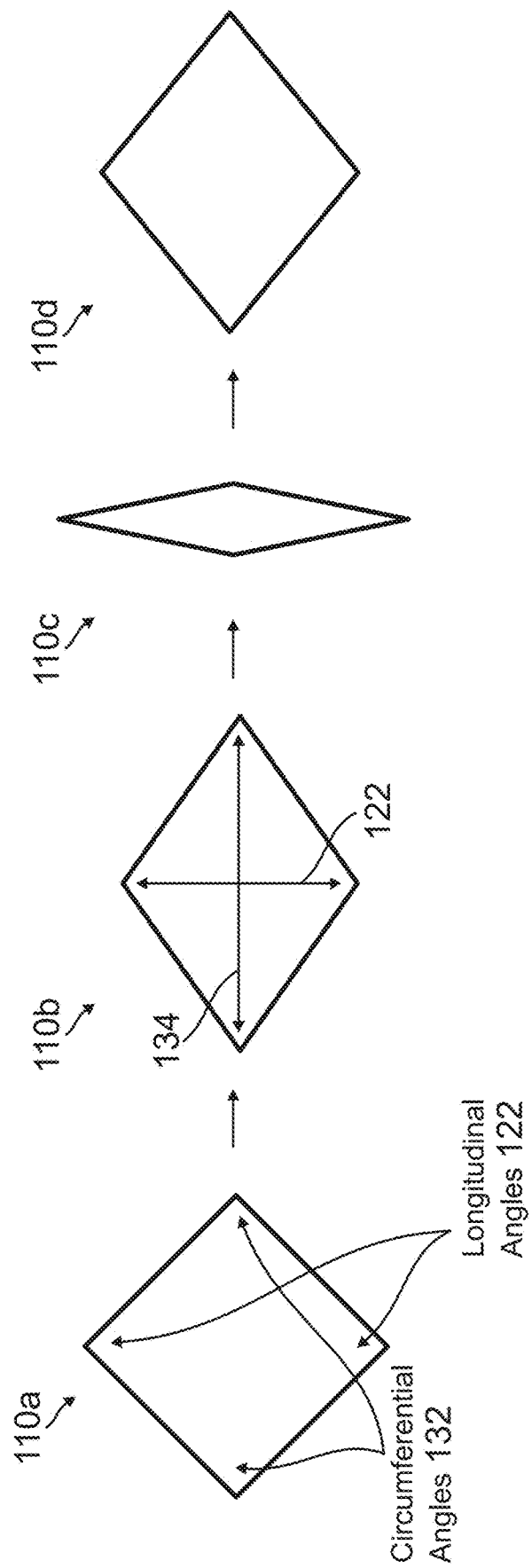

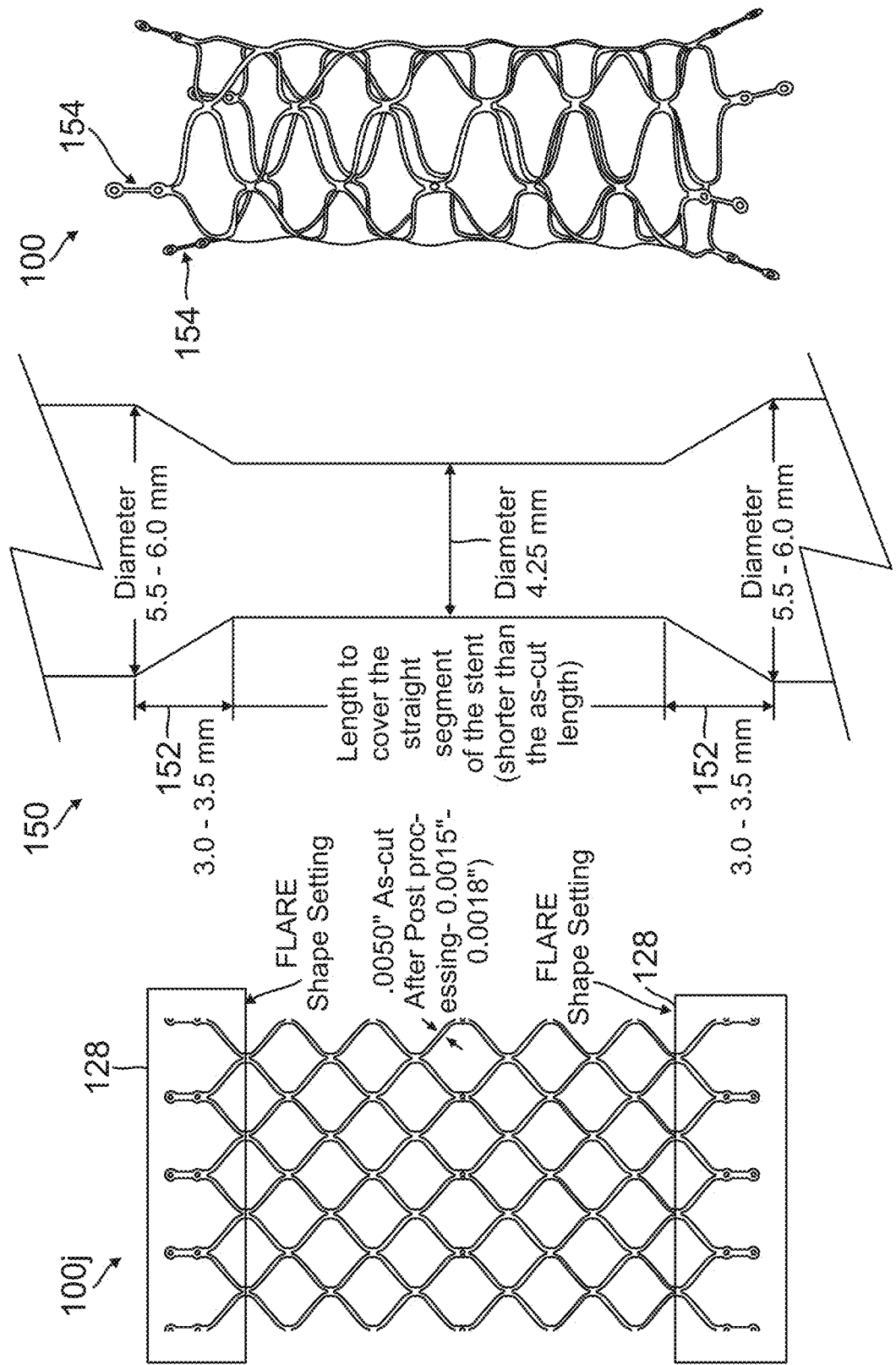

KINK-RESISTANT STENT DEVICES AND RELATED METHODS

The present application is a continuation of International Application No. PCT/US2017/025548, filed Mar. 31, 2017, which claims the benefit of U.S. Provisional Application No. 62/317,376, filed on Apr. 1, 2016, both of which are hereby incorporated by reference in their entirety.

TECHNICAL FIELD

The present disclosure relates to medical devices and, more particularly, to kink-resistant stent devices for treatment of tissue defects such as aneurysms.

BACKGROUND

Tissue defects involve an absence of healthy tissue in a body area where such tissue would normally be present. For example, a common tissue defect includes aneurysms, in which there is a defect in a blood vessel wall that causes an outpouching of the vessel tissue. Aneurysm may form in disparate locations such as the aorta, iliac arteries, renal arteries, popliteal arteries, splenic arteries, femoral arteries, tibial arteries, and throughout the neurovasculature. Other common tissue defects include arteriovenous fistulas, intestinal fistulas, colonic fistulas, anal fistulas, hernias and traumatic wounds. Aneurysms and other tissue defects may be treated using surgical methods, such as clipping, or endovascular methods, such as flow diversion techniques using a flow diverter (e.g., a covered stent) or coil embolization techniques using coils or a combination of coils and a stent.

In coil embolization techniques, small metallic coils are delivered to the sac of an aneurysm. The coils pack the sac densely to limit blood flow in the sac, thereby inducing clotting of the blood inside the sac and, eventually, healing of the aneurysm. However, such coil embolization techniques can be used only with aneurysms with a narrow neck region to hold the coil in place. Further, such coil embolization techniques suffer from complications, including the risk of recanalization in which blood flow returns to the sac and further swells the sac.

In coil embolization techniques using a combination of coils and a stent, the stent is used as a device that acts as a scaffolding structure to keep the coil inside the aneurysm volume. After the stent is deployed covering the neck of the aneurysm, a delivery microcatheter is passed through a strut (also called an element) of the stent into the aneurysm dome and embolic coils are deployed through the catheter tip inside the aneurysm dome to fill the aneurysm volume.

A significant problem with coil embolization techniques is that during the process of filling the aneurysm volume, the coils or blood clots at the embolization site sometimes herniate into the parent artery if the stent fails to provide adequate scaffolding. Coils or blood clots herniating into the parent artery may escape from the aneurysm volume and travel downstream into the blood vessel and cause a stroke or other life threatening complications.

Another technique for treating aneurysms is with the use of a flow diverting stent. A flow diverter is placed in a blood vessel such that it spans the neck region of an aneurysm, thereby diverting blood flow away from the aneurysm sac. The stagnant blood inside the aneurysm sac may then clot and the aneurysm may heal.

Flow diverters, however, also suffer from complications. Braided devices used in the neurovasculature are bulky and often cannot access distal aneurysms. Use of these devices may also result in incomplete or delayed aneurysm occlusion, which can lead to delayed aneurysm rupture and stroke. In other vascular beds, such as the aorta or arteries of the lower extremities, covered stents are used to treat aneurysms. The most commonly used materials for covered stents include polytetrafluorethylene (PTFE) and polyethylene terephthalate (PET). Both of these polymeric materials add substantial bulk, making the stent unsuitable for use in certain vascular beds, such as the neurovasculature. In addition, these materials tend to be impermeable or only semi-permeable. This limits tissue in-growth into the stent covering and leaves a foreign body that is continuously exposed to blood. Because of this, there is a long-term risk of acute thrombosis and stenosis inside the stent. Moreover, because these stents are impermeable to blood flow they will cut-off blood flow to any vessels adjacent to the aneurysm that are covered with the stent. This can lead to ischemia of critical tissues such as the intestine. Further, blood clots formed at the covered stent implanted site may dislodge and cause a heart attack, stroke, or other life threatening complications.

A significant problem with stents, whether used to provide scaffolding to coils in coil embolization techniques or as a covered stent in flow diversion techniques, is their tendency to kink and failing to achieve good wall apposition when placed in torturous vascular beds. Accordingly, there is a need in the art for improved stents that are more kink resistant and achieve improved wall apposition, while simultaneously serving as a good scaffold for coil-based aneurysm treatment techniques.

BRIEF DESCRIPTION OF THE DRAWINGS

FIG. 1A is a side view image of a stent according to an embodiment.

FIG. 1B is a side view image of a stent according to an embodiment.

FIG. 1C is a front view image of a stent according to an embodiment.

FIG. 2A is a diagrammatic flat pattern view of a 4-cell stent as cut from a hypotube according to an embodiment.

FIG. 2B is a diagrammatic flat pattern view of the stent of 2A after expansion and annealing according to an embodiment.

FIG. 3A is a diagrammatic flat pattern view of a 2-cell stent according to an embodiment.

FIG. 3B is a diagrammatic flat pattern view of a 3-cell stent according to an embodiment.

FIG. 4A is a diagrammatic flat pattern view of a symmetric 2-cell/4-cell hybrid stent according to an embodiment.

FIG. 4B is a diagrammatic flat pattern view of an asymmetric 2-cell/4-cell hybrid stent according to an embodiment.

FIGS. 6A-D illustrate an exemplary single cell of a stent in various stages (as cut from hypotube, after annealing, as crimped into a catheter, and as deployed) according to an embodiment.

FIG. 9A is a diagrammatic flat pattern view of a stent showing areas at the ends to be flared according to an embodiment.

FIG. 9B is a diagrammatic cross-sectional view of a shape set mandrel for facilitating flared ends to a stent according to an embodiment.

FIG. 9C is a diagrammatic side view of a stent with flared ends according to an embodiment.

Figure 5C:
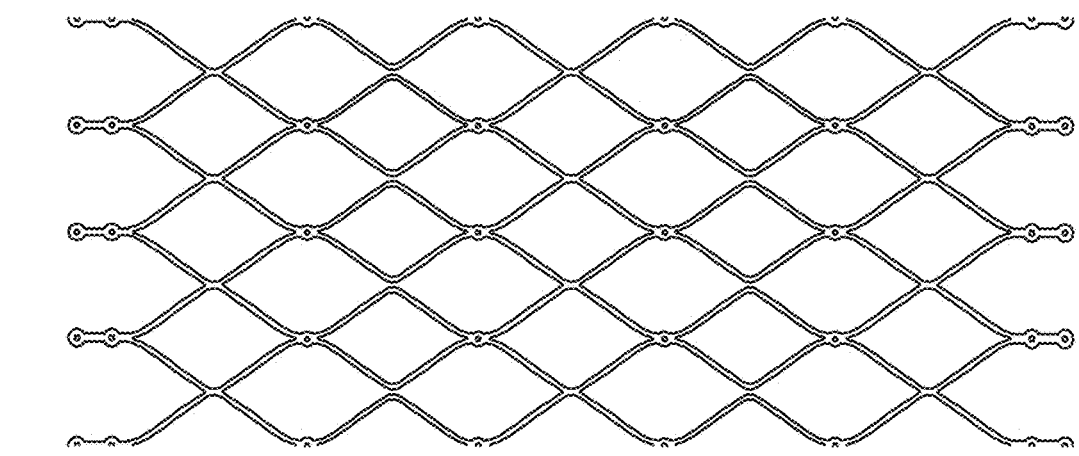
FIG. 5C is a diagrammatic flat pattern view of a 4-cell stent including free cells according to an embodiment.

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

FIG. 1A is a side view of a stent 100 in its relaxed state (e.g., its expanded and annealed state). Stent 100 is tubular and has a cylindrical shape. Stent 100 is highly elastic and flexible such that it is highly kink-resistant when deployed in tortuous blood vessels. Further, stent 100 is self-expandable so that it may be compacted into a delivery catheter and when deployed from the delivery catheter inside a blood vessel, stent 100 expands to its relaxed state or to the diameter of a blood vessel. Stent 100 is further shown in FIGS. 1B and 1C. For example, stent 100 may be a 4-cell stent with four cells per row (as shown in FIG. 1A), a 3-cell stent with three cells per row (as shown in FIGS. 1B-C), or a 2-cell stent with two cells per row.

Figure 14:
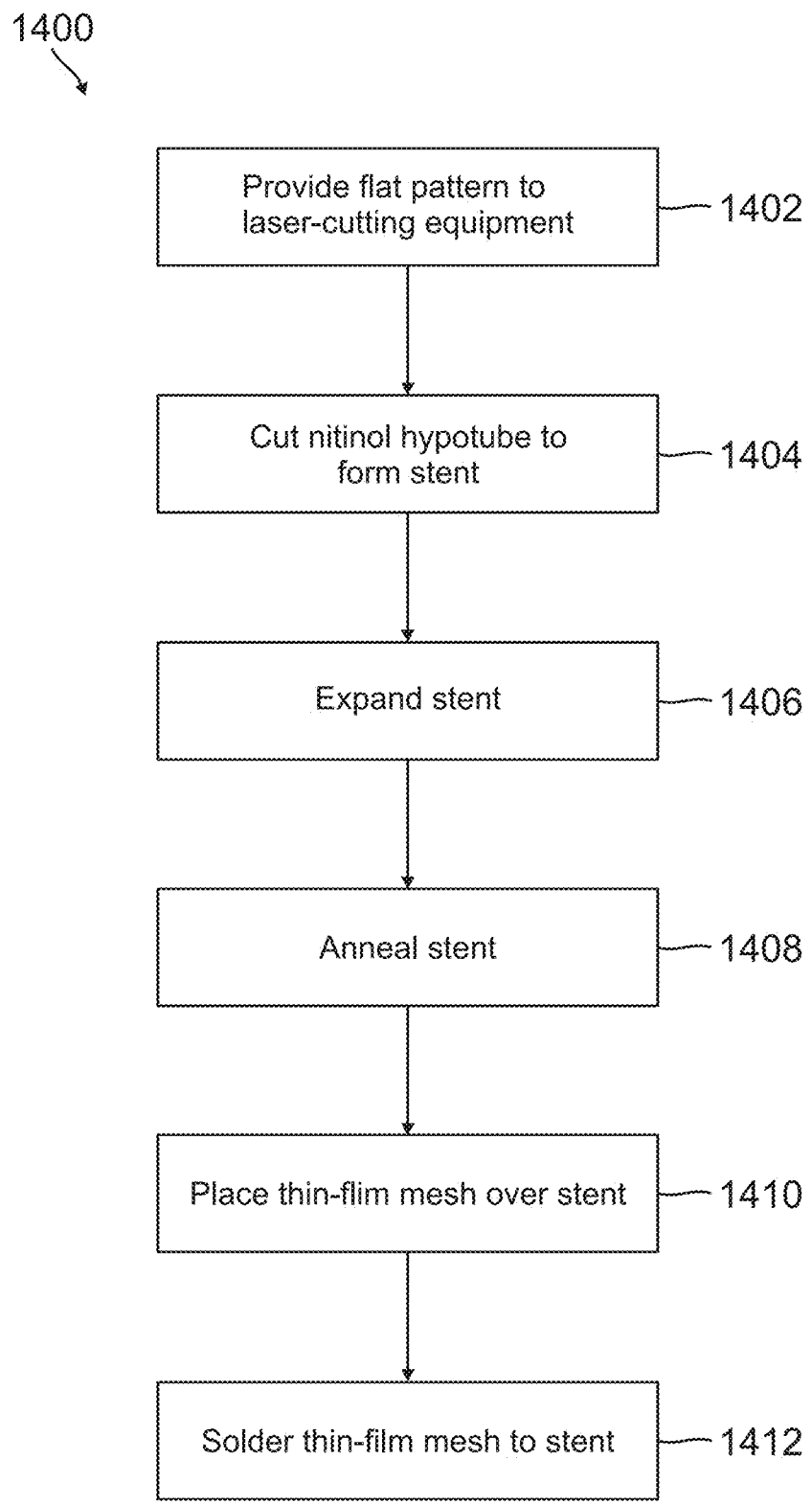
FIG. 14 illustrates a method of fabricating a stent device according to an embodiment.

Stent 100 comprises a plurality of cells 110 (e.g., apertures, holes, openings, fenestrations, etc.) formed by a plurality of struts 112. Stent 100 has a longitudinal direction or a longitudinal axis 120, as shown in FIGS. 1A and 1B. Further, stent 100 has a circumferential direction or a circumferential axis 130 along the outer surface of stent 100 and orthogonal to longitudinal direction 120, as shown in FIGS. 1A and 1C. Cells 110 are arranged in a plurality of rows extending along circumferential direction 130 (i.e., rows around stent 100), and a plurality of columns extending along longitudinal direction 120 (i.e., columns along the length of stent 100). Struts 112 may be composed of a superelastic alloy such as an alloy of Nickel and Titanium, also called nitinol. Struts 112 may be formed by laser cutting cells 110 on a hypotube (as shown in FIG. 14 and further described below.)

As shown in FIG. 1A and further illustrated by a flat pattern 100b of stent 100 shown in FIG. 2B (which is how stent 100 would look like if cut along a longitudinal line 128 of FIGS. 1A and 1B and then pressed flat), each cell 110 has a length 124 along longitudinal direction 120, and a width 134 along circumferential direction 130. Width 134 is longer than length 124 when stent 100 is in its relaxed state. The ratio of width 134 to length 124 (width 134/length 124) is greater than 1. The ratio of width 134 to length 124 may be exactly or approximately 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, and 3.5, where any value can form an upper end point or a lower end point of a range for the ratio, as appropriate. For example, the ratio of width 134 to length 124 may be between 1.2 and 3, between 1.2 and 2.5, between 1.5 and 3, or between 1.5 and 2.5.

As shown in FIGS. 1A and 2B, each cell 110 may have an angle at each end along longitudinal direction 120, referred to as longitudinal angle 122. Cells 110 may also have an angle at each end along circumferential direction 130, referred to as circumferential angle or radial angle 132. Longitudinal angle 122 and/or circumferential angle 132 may be an angle formed by hypothetical lines extending from straight or substantially straight portions of the two struts 112 forming the respective angle (e.g., before struts 112 curve toward each other to join). Longitudinal angle 122 is larger than circumferential angle 132 in its relaxed state.

As shown in FIGS. 1B and FIG. 2B, each cell 110 is surrounded by four struts 112 (112a, 112b, 112c, and 112d). First strut 112a extends from a first cusp 126a at one end of cell 110 along longitudinal direction 120 to a first U-shaped side 136a of cell 110, second strut 112b extends from first U-shaped side 136a to a second cusp 126b at an opposing end of cell 110 along longitudinal direction 120, third strut 112c extends from second cusp 126b to a second U-shaped side 136b of cell 110 opposing first U-shaped side 136a, and fourth strut 112d extends from second U-shaped side 136b to first cusp 126a. Each cell 110 may have a substantially quadrilateral shape, a substantially parallelogram shape, a substantially diamond (rhombus) shape, a substantially square shape, and may include one or more curved sides (e.g., U-shaped sides 136a, 136b). The kink-resistance of stent 100 is due to this symmetric, diamond-like shape and the dimensions of cells 110.

Stent 100 may be made from a hypotube of a superelastic alloy, such as a nitinol hypotube. The design of stent 100 is first drawn as a flat pattern 100a as shown in FIG. 2A, which is how stent 100, before it is expanded and annealed as further described below, would look if cut along longitudinal line 128 and then pressed flat. Flat pattern 100a may be drawn, for example, on a Computer-Aided-Design (CAD) system or software. The same design pattern 100a of stent 100 is then formed on the hypotube by cutting the design pattern onto the hypotube using a powerful laser beam.

Cut-out parts of the hypotube are removed to form cells 110 surrounded by struts 112. In an example, when the stent is laser cut from a Nitinol hypotube, all angles of cells 110—longitudinal angles 122 and circumferential angles 132—may all be equal (90 degrees) or approximately equal (approximately 90 degrees). In other examples, the angles of cells 110 may include an angle of 70 degrees, 75 degrees, 80 degrees, 85 degrees, 95 degrees, 100 degrees, 105 degrees, 110 degrees, where any value can form an upper end point or a lower end point of a range for the angle, as appropriate.

Laser-cut stent 100 is expanded and annealed on a mandrel with a larger diameter than the original hypotube to form stent 100 with its final specification as described herein. This shortens stent 100 along the longitudinal direction 120 and expands cells 110 along the circumferential direction 130, while at the same time making circumferential angle 132 of cells 110 more acute, and longitudinal angles 122 more obtuse. Flat pattern 100b of the final expanded and annealed stent 100 is shown in FIG. 2B, which is how stent 100 would look if cut along longitudinal line 128 of FIGS. 1A and 1B and then pressed flat.

Figure 11A:
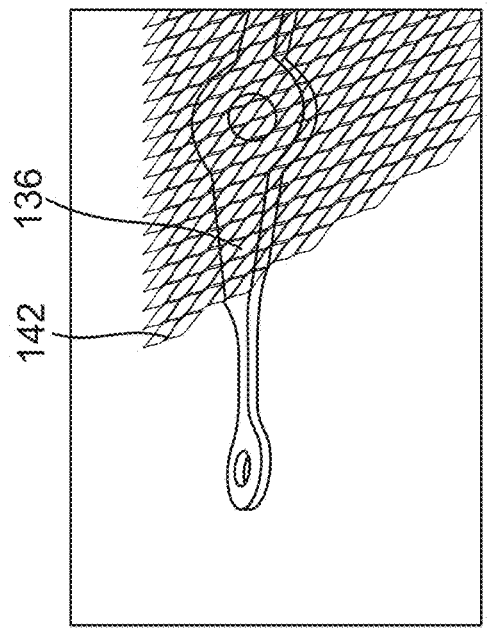
FIGS. 11A-C are images of solder holes for affixing a thin-film mesh stent cover according to an embodiment.
Figure 11B:
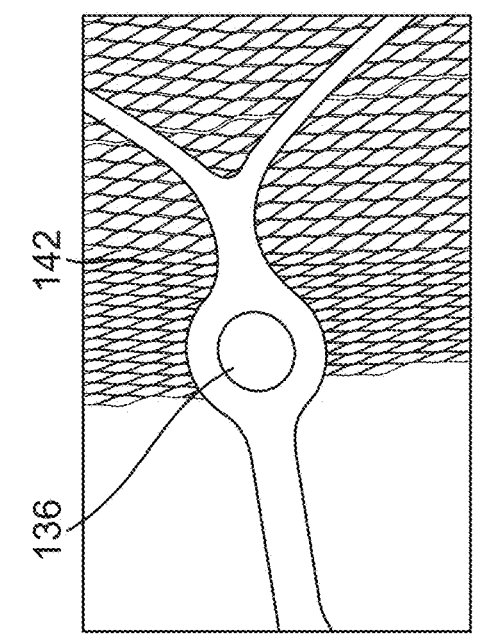
Figure 11C:
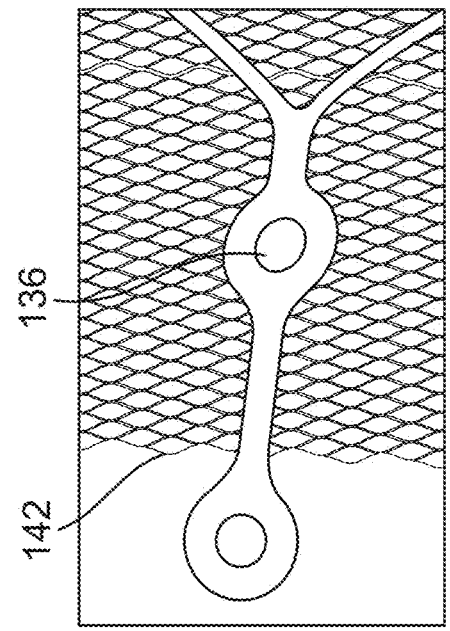

In some embodiments, during the expansion and annealing, one or more longitudinal end regions 128 may be flared (as shown in FIGS. 9A-C and further described below). In some embodiments, stent 100 includes one or more solder holes 136. For example, solder holes may be disposed around circumferential direction 130 at longitudinal end regions 128 and/or a region in the middle of stent 100 (as shown in FIGS. 11A-C and further described below).

Once expanded and annealed, stent 100 advantageously has a high amount of kink-resistance because the acute circumferential angle 132 can easily stretch to accommodate a curve. Also, stent 100 advantageously has increased radial force with a relatively small amount of metal. The radial force is increased because when stent 100 is crimped, the elastic struts of stent 100 are deformed to be more parallel to longitudinal direction 120 and, thereby, storing more potential energy. This is important for fitting stent 100 into a small microcatheter and deploying stent 100 in a blood vessel.

Stent 100 shown in FIGS. 2A and 2B has four cells 110 for each row extending along circumferential direction 130 such that stent 100 has four columns, each column extending along longitudinal direction 120. In another example, stent 100 fabricated using a flat pattern 100c as shown in FIG. 3A (representing stent 100 sliced longitudinally and pressed flat before stent 100 is expanded and annealed) has two cells 110 for each row along circumferential direction 130 such that stent 100 has two columns along longitudinal direction 120. In a further example, stent 100 fabricated using a flat pattern 100c shown in FIG. 3B (representing stent 100 sliced longitudinally and pressed flat before stent 100 is expanded and annealed) has three cells 110 for each row along circumferential direction 130 such that stent 100 has three columns along longitudinal direction 120.

Stent 100 with the 4-cell design advantageously experiences less foreshortening when deployed compared to stent 100 with the 2-cell design or the 3-cell design. Further, stent 100 with the 4-cell design covered with a thin-film mesh experiences less prolapse of the thin-film mesh when deployed (particularly around the bends) than stent 100 with the 2-cell or the 3-cell design. Stent 100 with the 2-cell design or the 3-cell design may be optimal for smaller vessels because they have less material and would allow delivery via smaller catheters. Further, stent 100 with the 2-cell design or the 3-cell design covered with a thin-film mesh may experience less prolapse of the thin-film mesh when deployed in smaller vessels (e.g., the thin-film mesh may be stretched in longitudinal direction 120 due to stent 100 being expanded along longitudinal direction 120 and contracted along circumferential direction 130 relative to its relaxed state to fit the narrow vessel).

In yet further examples, stent 100 may have more than four cells for each row along circumferential direction 130. However, stent 100 with more than four cells for each row is less kink-resistant so may be less suitable for torturous vessels. Further, stent 100 with more than four cells for each row may have too much material to fit into a microcatheter (e.g., one which has an inner diameter of 0.027 inch), especially if stent 100 is covered with a thin-film mesh.

Flat patterns 100a of FIGS. 2A, 3A, and 3B have an equal number of cells 110 for each row of cells 110 around circumferential direction 130. Alternatively, stent 100 includes at least one row of cells 110 around circumferential direction 130 having a different number of cells 110 from the remaining rows of cells 110. For example, stent 100 may have a 2-cell and 4-cell hybrid design with flat pattern 100e, 100f as shown in FIGS. 4A and 4B (representing stent 100 sliced longitudinally and pressed flat before stent 100 is expanded and annealed).

FIG. 4A shows flat pattern 100e of a symmetric 2-cell/4-cell hybrid stent 100 in which regions on either side (including longitudinal end regions 128) have two cells per row along circumferential direction 130 and a middle region has four cells per row along circumferential direction 130. Longitudinal end regions 128 having two cells per row facilitate flaring (as shown in FIGS. 9A-C and further described below). The middle region having four cells per row provides a scaffold for a thin-film mesh stent cover.

FIG. 4B shows flat pattern 100f of an asymmetric 2-cell/4-cell hybrid stent 100 in which a first region/portion has four cells per row along circumferential direction 130 and a second region has two cells per row along circumferential direction 130. A thin-film mesh stent cover may be placed over only the 4-cell region and be advantageously used in various aneurysm treatment methods (such as the methods shown in FIGS. 12 and 13 and described further below).

Figure 5B:
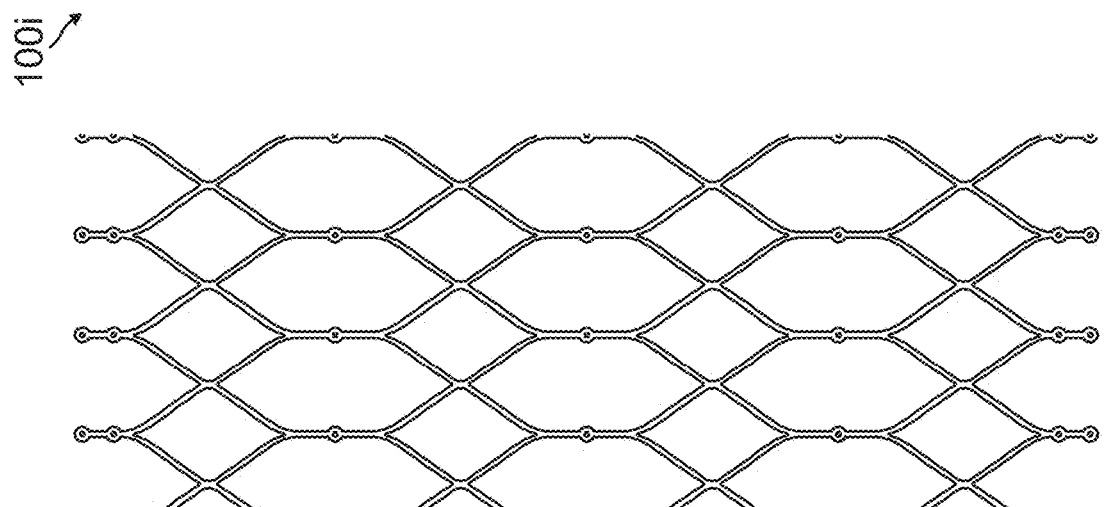
FIG. 5B is a diagrammatic flat pattern view of a 4-cell stent with extended interconnects according to an embodiment.
Figure 5A:
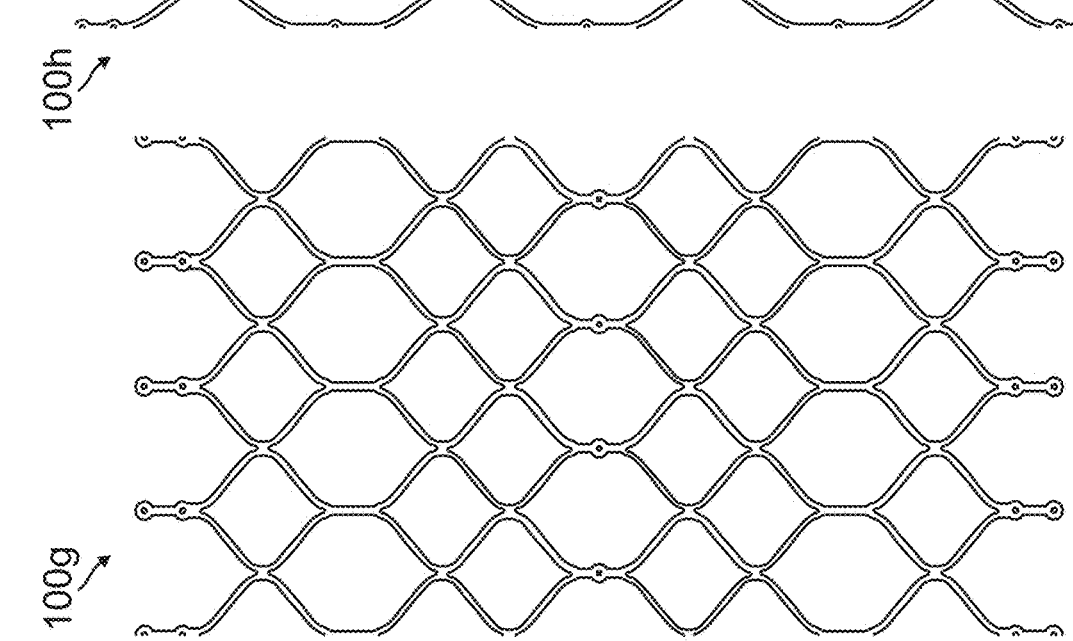
FIG. 5A is a diagrammatic flat pattern view of a 4-cell stent with extended interconnects according to an embodiment.

In further examples, stent 100 may have cells 110 with long interconnects (e.g., the struts surrounding cells may extend to form interconnects) with flat pattern 100g, 100h as shown in FIGS. 5A and 5B (representing stent 100 sliced longitudinally and pressed flat). Advantageously, stent 100 with long-interconnect design has reduced foreshortening when deployed and reduced total amount of metal in stent 100. However, stent 100 with long-interconnect design may be less kink-resistance due to the interconnects.

In yet a further example, stent 100 may have cells 110 that are "free" or "open" every other row around circumferential direction 130 such that two adjacent cells are connected as illustrated by flat pattern 110i shown in FIG. 5C (representing stent 100 sliced longitudinally and pressed flat). Stent 100 with free cells every other row has reduced foreshortening when deployed.

FIGS. 6A-D illustrate one exemplary cell 110 of stent 100 in various stages/states. FIG. 6A shows cell 110a when stent 100 is laser-cut from the hypotube. Longitudinal angles 122 and circumferential angles 132 are equal or approximately equal.

FIG. 6B shows cell 110b after stent 100 is extended and annealed on a mandrel having a larger diameter than the hypotube. Longitudinal angles 122 are now obtuse (greater than 90 degrees), which provides good radial force when crimped and circumferential angles 132 are now acute (less than 90 degrees), which provides high kink-resistance because stent 100 can stretch along longitudinal direction 120. After stent 100 is expanded and annealed, stent 100 has a relaxed state in which cells 110 have longitudinal angle 122 that is larger than circumferential angle 132, and have length 124 that is shorter than width 134.

FIG. 6C shows cell 110c when stent 100 is crimped into a small diameter catheter. When stent 100 is in its crimped state, cells 110 have longitudinal angle 122 that is smaller than circumferential angle 132, and have length 124 that is longer than width 134. Stent 100 exerts good radial force even with small amount of material because potential energy is stored when the longitudinal angles 122 of stent 100 is increased by crimping stent 100. Stent 100 exerts radial force to return to its relaxed state, which helps stent deploy properly.

FIG. 6D shows cell 110d when stent 100 is deployed in a blood vessel. When stent 100 is deployed, cell 110d comes back to its relaxed state and stent 100 conforms to the vessel wall.

Figure 7A:
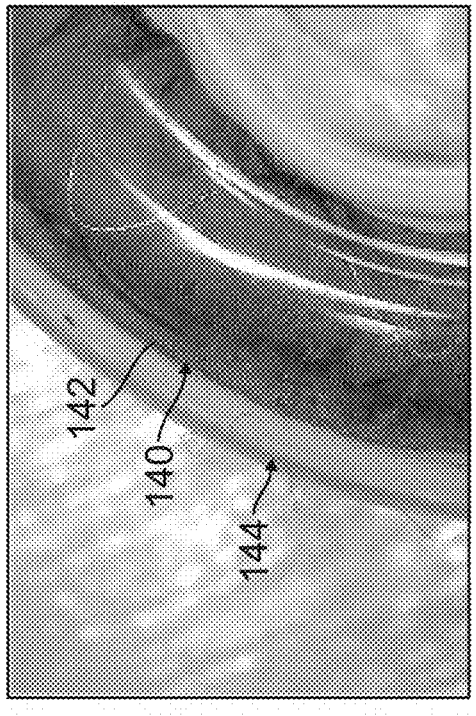
FIGS. 7A-B are images of a device with a 4-cell stent and a thin-film mesh stent cover deployed in a simulated curved vessel according to an embodiment.
Figure 7B:
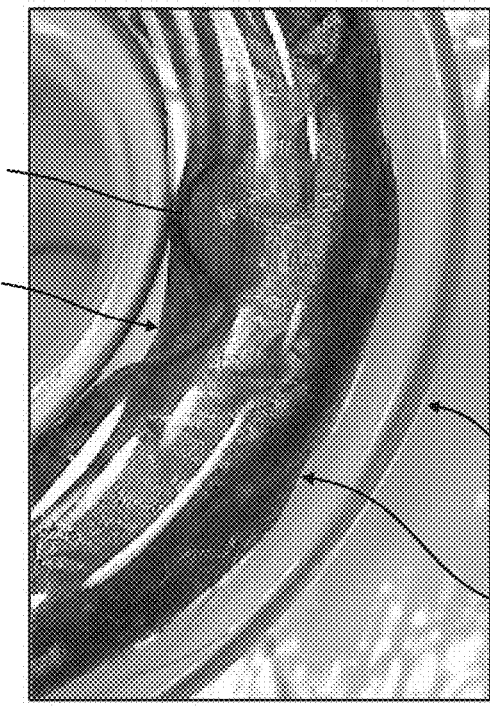
Figure 8A:
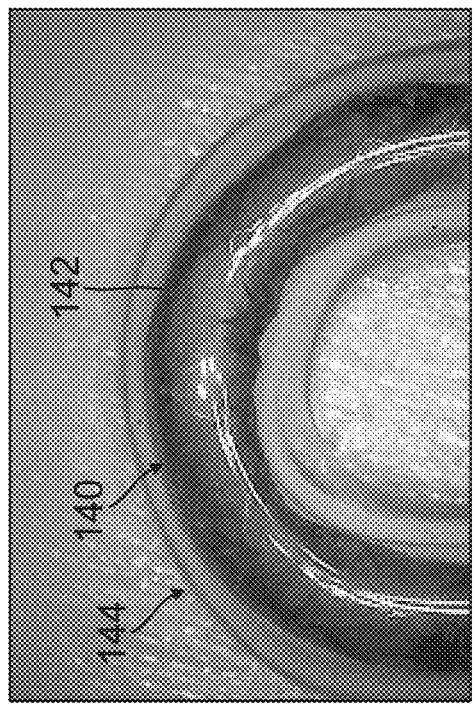
FIGS. 8A-B are images of a device with a 3-cell stent and a thin-film mesh stent cover deployed in a simulated curved vessel according to an embodiment.
Figure 8B:
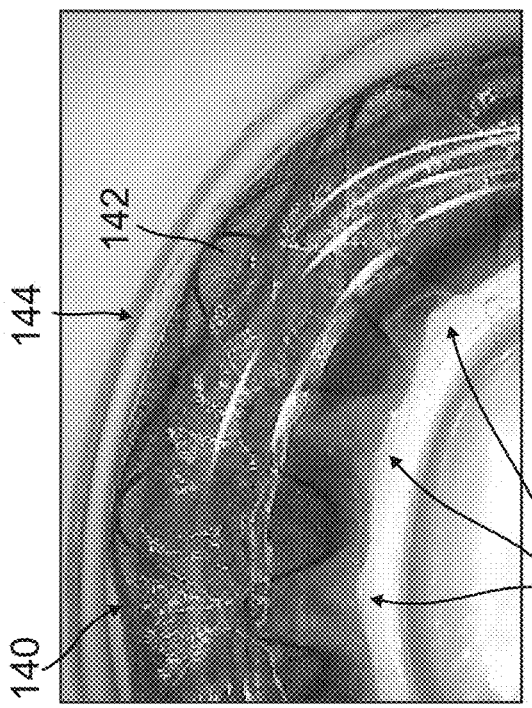

FIGS. 7A-B are images of a device 140 including stent 100 with a 4-cell design and a thin-film mesh stent cover 142 deployed in a simulated curved vessel 144. Advantageously, device 140 using 4-cell design of stent 100 shows no thin-film 142 prolapsing into the lumen and high kink-resistance. FIGS. 8A-B are images of device 140 including stent 100 with a 3-cell design and thin-film mesh stent cover 142 deployed in simulated curved vessel 144. Device 140 using 3-cell design of stent 100 shows thin-film 142 prolapsing into the lumen at various areas 146. Stent 100 with the 4-cell design advantageously minimizes prolapsing of thin-film 142 when deployed compared to Stent 100 with the 3-cell design, while Stent 100 with the 3-cell design advantageously provides even higher kink resistance and allows delivery via smaller catheters compared to Stent 100 with the 4-cell design.

Stent 100 may have flared ends at one or both longitudinal end region 128 of stent 100. FIG. 9A is a flat pattern view 100j showing areas 128 to be flared. FIG. 9B is a diagrammatic cross-sectional view of a shape set mandrel 150 for providing flared ends to stent 100. Mandrel 150 may have a diameter that is larger than the diameter of the hypotube used to form stent 100 (the diameter of stent 100 before expanding and annealing.) Mandrel 150 further includes a flare region 152 in which the diameter increases (e.g., flares). For example, flare region 152 of mandrel 150 may provide flared ends to stent 100 at a region between 3.0 mm and 3.5 mm from the longitudinal end of stent 100. FIG. 9C is a diagrammatic side view of stent 100 with flared ends 154.

Figure 10B:
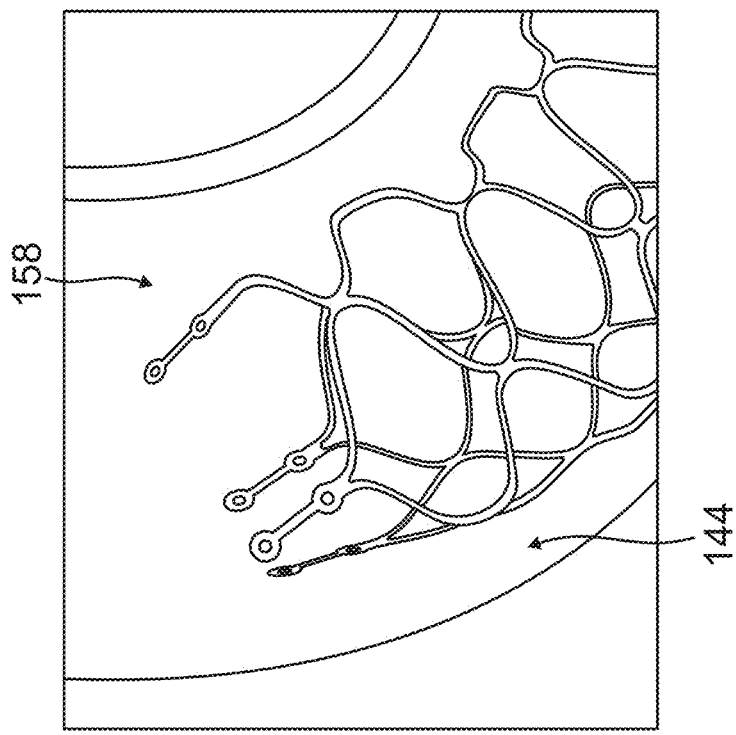
FIG. 10B is an image of a stent without flared ends deployed in a simulated curved vessel according to an embodiment.
Figure 10A:
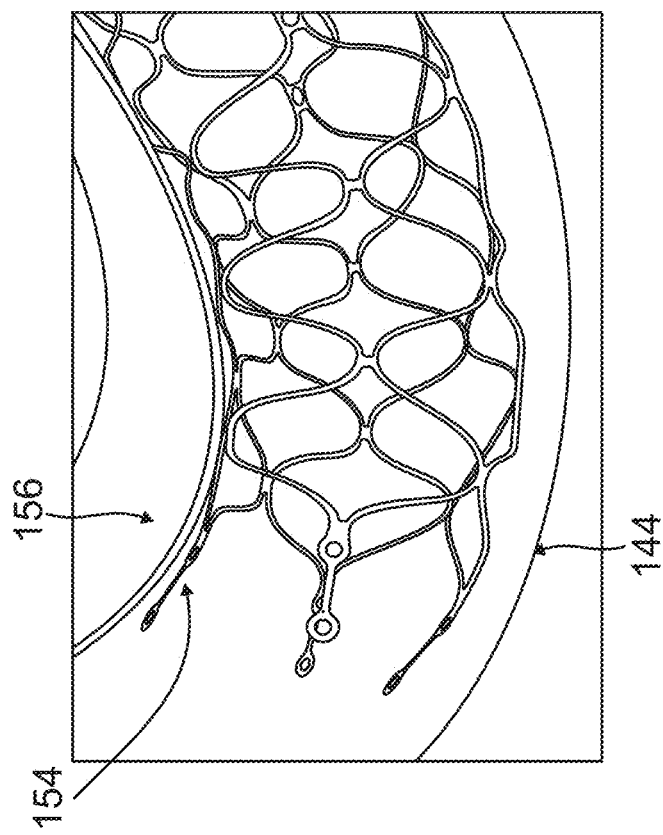
FIG. 10A is an image of a stent with flared ends deployed in a simulated curved vessel according to an embodiment.

FIG. 10A is an image of stent 100 with flared ends 154 and FIG. 10B is an image of stent 100 without flared ends, each deployed in simulated curved vessel 144. As shown in FIG. 10A, end 156 of stent 100 with flared ends 154 conforms to vessel wall due to flared ends 154. As shown in FIG. 10B, end 158 of stent 100 without flared ends are not apposed around curve.

Stent 100 may include solder holes 136 that may be used as reservoirs to hold solder that attaches (e.g., affix) stent 100 to thin-film mesh stent cover 142 as shown in FIGS. 11A-C. A low melting temperature solder may be used without damaging thin-film mesh stent cover 142 (e.g., a nitinol thin-film mesh stent cover). Solder holes 136 may be disposed at strategic locations (e.g., proximal, middle, distal portion of stent 100).

Figure 12:
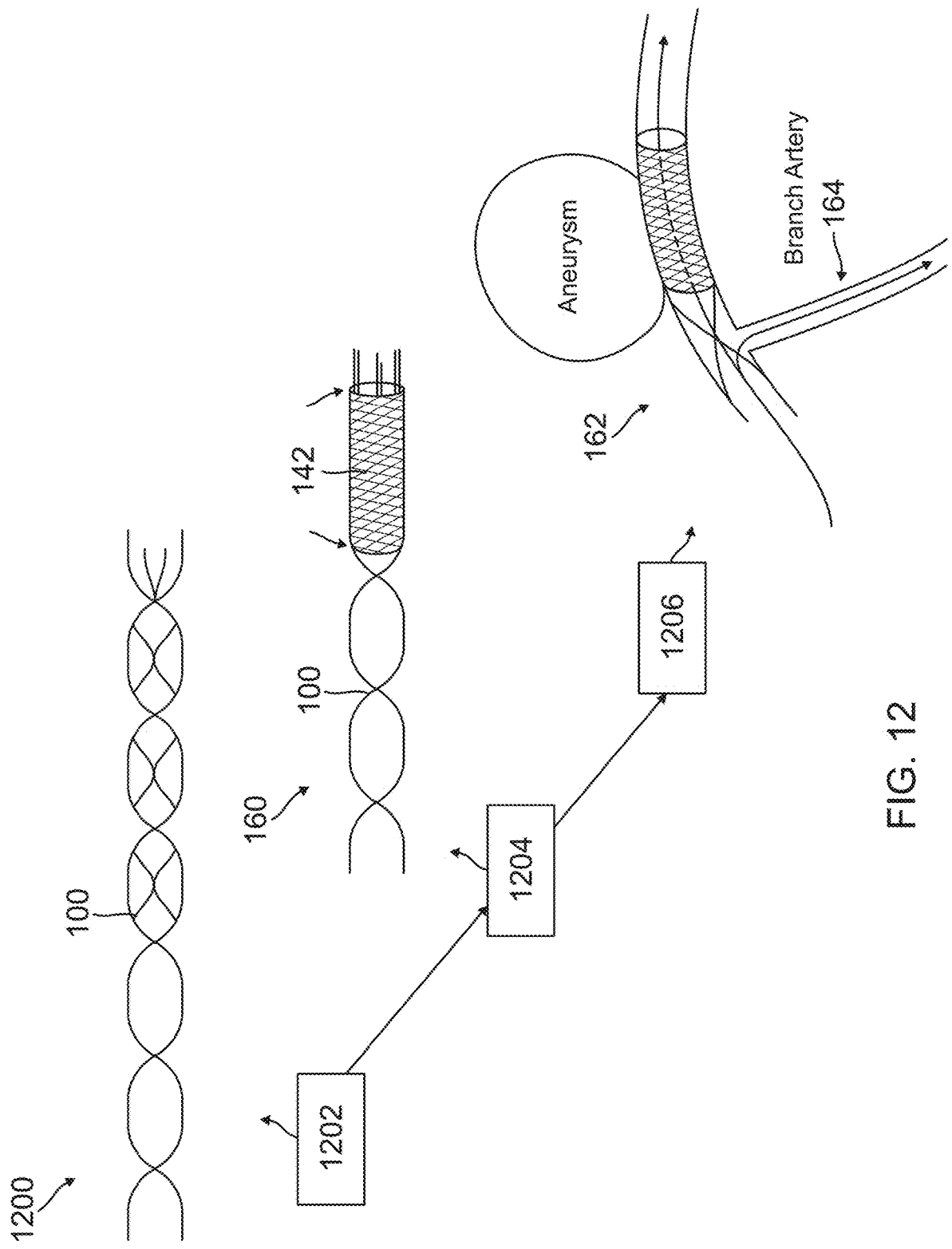
FIG. 12 illustrates a method for forming and deploying a covered stent at an aneurysm site according to an embodiment.

FIG. 12 illustrates a method 1200 for forming and deploying a covered stent device such as device 160 including stent 100 and thin-film mesh stent cover 144 at an aneurysm site. At block 1202, stent 100 which may have an asymmetric 2-cell/4-cell hybrid design, may be formed from a nitinol hypotube. At block 1204, 4-cell portion of stent 100 is covered with thin-film mesh stent cover 144 to form device 160. At block 1206, device 160 is deployed at aneurysm site 162. Advantageously, by positioning device 160 such that the 2-cell portion of stent 100 covers a branch artery 164, flow to branch artery 164 is preserved.

Figure 13:
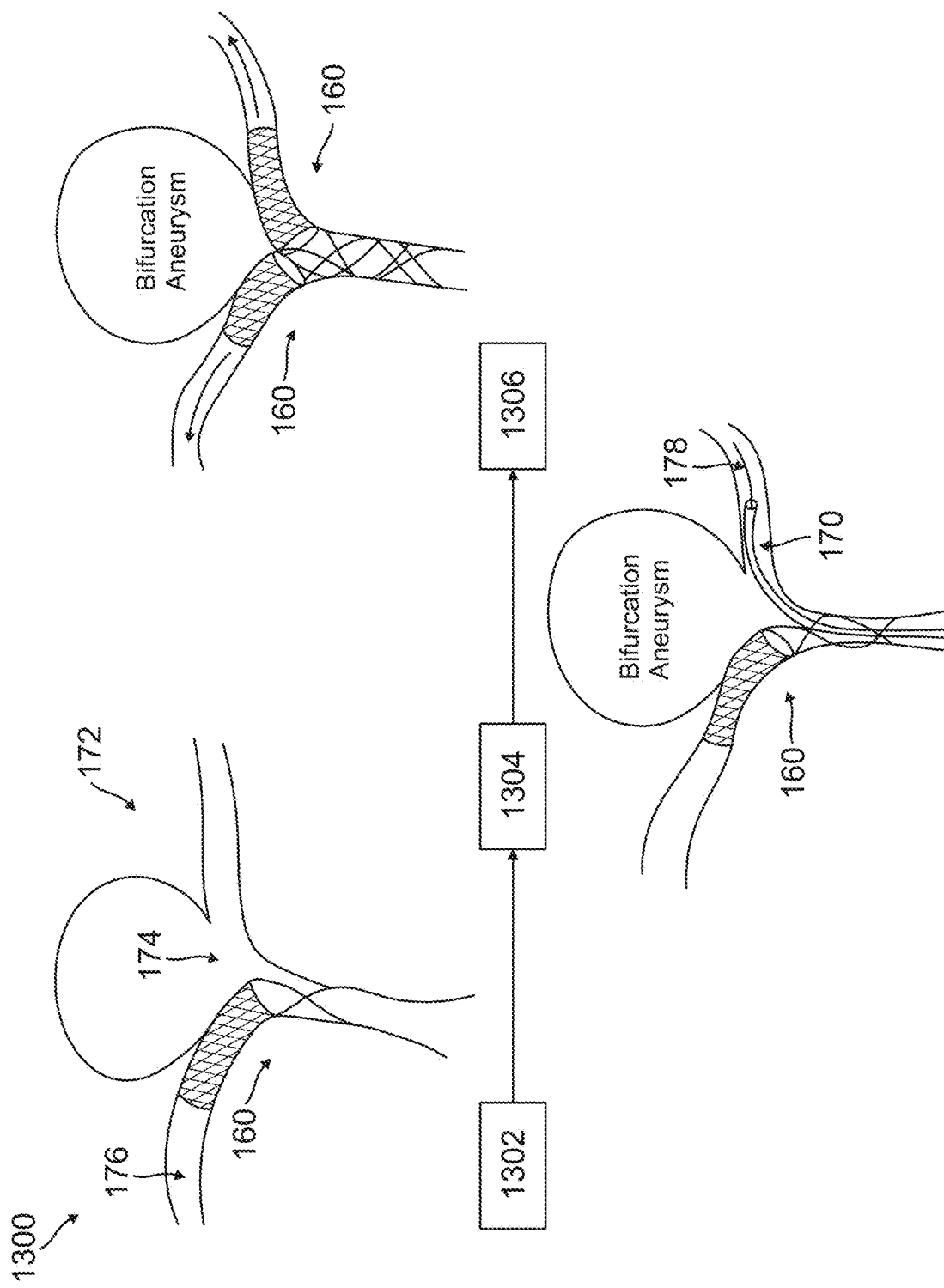
FIG. 13 illustrates a method for deploying a covered stent at a bifurcated aneurysm site according to an embodiment.

FIG. 13 illustrates a method 1300 for deploying a covered stent such as device 160 at a bifurcated aneurysm site. Devices 160 may be prepared according to blocks 1202 and 1204 in FIG. 12 as described above. At block 132, first device 160 is deployed using a catheter 170 at a bifurcated aneurysm site 172 such that the 4-cell portion of stent 100 with thin-film mesh 144 covers a portion of a neck 174 of bifurcated aneurysm 172 and is apposed to a first branch artery 176 of bifurcated aneurysm 172. At block 1304, catheter 170 is advanced through 2-cell portion of stent 100 into a second branch artery 178 of bifurcated aneurysm 172. Accordingly, the 2-cell portion of stent 100 provides an open structure through which to advance a guidewire and catheter 170. At block 1306, second device 160 is deployed using catheter 170 at bifurcated aneurysm site 172 such that the 4-cell portion of stent 100 with thin-film mesh 144 covers the remaining portion of neck 174 of bifurcated aneurysm 172 and is apposed to the wall of second branch artery. Tissue will grow over thin-film mesh stent cover 144 to form a complete barrier at neck 174 of bifurcated aneurysm 172.

FIG. 14 illustrates a method 1400 of fabricating a stent device that includes a stent backbone such as stent 100. To fabricate stent 100, first a flat pattern (e.g., as shown in 100a-i in FIGS. 2A-B, 3A-B, 4A-B, and 5A-C) of the stent 100 is drawn using a CAD system or software (e.g., AutoCAD). The width of the struts of cells 110 in flat pattern 100a-i may be between, for example, 0.0030 inches to 0.0050 inches. The specification of the strut width depends on the wall thickness of the nitinol hypotube from which stent 100 is cut. At block 1402, flat pattern 100a-i is provided to laser-cutting equipment such as by programming flat pattern 100a-i into a computerized laser-cutting equipment.

At block 1404, the laser-cutting equipment drives a powerful laser beam along the edges of the design in flat pattern 100a-i and thereby cuts the pattern on the nitinol hypotube to form stent 100 in its laser-cut form, which includes a plurality of struts 112 that form a plurality of cells 110. Cells 110 may be diamond-shaped, and have longitudinal angle 122 that is approximately equal to circumferential angle 132. Laser-cut stent 100 may go through one or more subsequent processes such as stress-relief heat treatment at a high temperature (e.g., 500° C.) to remove stress from the laser-cut parts and/or microblasting to remove the outside oxide layer.

At block 1406, laser-cut stent 100 is expanded and annealed to set the shape of stent 100. Laser cut stent 100 may be expanded radially (e.g., by placing over a mandrel such as mandrel 150 shown in FIG. 9B and discussed above) such that longitudinal angle 122 of cells 110 is greater than 90 degrees (obtuse) and circumferential angle 132 is less than 90 degrees (acute). At block 1408, expanded stent 100 is annealed at a high temperature (e.g., 500° C.) for shape setting of stent 100. Further subsequent processes may be performed on stent 100, such as chemical etching and/or electro-polishing to remove some of the hypotube material to obtain stent 100 in its final product form. Stent 100 provides excellent kink resistance and conforms to tortuous anatomy as a result of the geometry of cells 110. Further, stent 100 provides excellent radial force with small amount of material, which facilitates stent deployment, also as a result of the geometry of cells 110.

In some examples, stent 100 in its final product form may have a longitudinal length of between 10 mm and 60 mm, a diameter of between 2 mm and 7 mm, and a strut width of between 0.0005 inches and 0.003 inches depending upon the degree of flexibility desired. One skilled in the art will appreciate that stent 100 may be constructed with other dimensions and specifications.

At block 1410, a thin-film mesh stent cover, which may be a cylindrical thin-film mesh tube, is placed over at least a part of stent 100. At block 1412, a low melting temperature solder may be applied to the thin-film mesh stent cover and stent 100 at solder holes 136, which serves as a reservoir for the low-melting temperature solder. Accordingly, thin-film mesh stent cover is attached over stent 100.

One or more of blocks 1402-1412 may be omitted, and blocks 1402-1412 may be performed in the provided order or in another order in alternative embodiments. Further, one or more processes, such as the subsequent processes discussed above or other processes, may be performed in between two of blocks 1402-1412.

Embodiments described herein illustrate but do not limit the disclosure. It should also be understood that numerous modifications and variations are possible in accordance with the principles of the present disclosure. Accordingly, the scope of the disclosure is best defined only by the following claims.

What is claimed is:

1. A device comprising:
   a self-expanding tubular stent extending in a longitudinal direction, the self-expanding tubular stent comprising:
   a plurality of struts forming a plurality of closed cells arranged in rows around the self-expanding tubular stent in a circumferential direction,
   wherein each of the rows comprises two to four closed cells, and wherein the closed cells of at least one of the rows are substantially equilateral cells, and
   wherein, in an expanded state, each of the closed cells has a width in the circumferential direction greater than a length in the longitudinal direction, and has a longitudinal angle that is obtuse and a circumferential angle that is acute.

2. The device of claim 1, wherein a ratio of the width to the length is between 1.5 and 3.

3. The device of claim 1, wherein the stent is formed from a nitinol hypotube.

4. The device of claim 1, wherein each of the rows comprises an equal number of the closed cells.

5. The device of claim 1, wherein each of the rows comprises four of the closed cells.

6. The device of claim 1, wherein of the rows comprises three of the closed cells.

7. The device of claim 1, wherein each of the rows comprises two of the closed cells.

8. The device of claim 1, wherein each of the rows comprises a different number of the closed cells.

9. The device of claim 1, wherein the stent is configured to be crimped to a smaller diameter, such that an outward radial force is stored when crimped.

10. The device of claim 1, wherein one or more of the struts at one or both end regions of the stent in the longitudinal direction are flared.

11. The device of claim 1, wherein the stent further comprises a plurality of solder holes disposed at one or more struts at one or both end regions of the stent in the longitudinal direction.

12. The device of claim 11, further comprising a thin-film tubular mesh attached to the solder holes by one or more solders.

13. The device of claim 1, wherein at least some of the struts extend to form long interconnects, and
   wherein the closed cells of at least one pair of the rows are connected together via the long interconnects.

14. A method, comprising:
   cutting a nitinol hypotube to form a stent with a plurality of quadrilateral cells, the plurality of quadrilateral cells arranged in rows along a circumferential direction of the stent, and wherein the quadrilateral cells in at least one of the rows are substantially equilateral cells;
   expanding the stent radially such that widths of the quadrilateral cells in the circumferential direction are greater than lengths of the quadrilateral cells in a longitudinal direction of the nitinol hypotube, and such that longitudinal angles of the quadrilateral cells are obtuse and circumferential angles of the quadrilateral cells are acute; and
   annealing the stent to fix a shape of the stent.

15. The method of claim 14, wherein a ratio of the widths to the lengths is between 1.5 and 3.

16. The method of claim 14, wherein the cutting comprises cutting the nitinol hypotube to form two, three, or four quadrilateral cells for each row.

17. The method of claim 14, wherein the cutting comprises cutting the nitinol hypotube to form different number of quadrilateral cells for different rows.

18. The method of claim 14, wherein the cutting comprises cutting one or both of longitudinal ends of the nitinol hypotube to form flared ends of the stent.

19. The method of claim 14, further comprising:
   placing a nitinol thin-film tubular mesh over the quadrilateral cells of the stent; and
   affixing the thin-film tubular mesh to the stent by soldering the thin-film tubular mesh at solder holes of the stent.

20. The method of claim 19, further comprising: crimping the stent to reduce a diameter of the stent; and storing the stent in a catheter.

21. The method of claim 20, further comprising deploying the stent from the catheter in a blood vessel.

* * * * *